United States Patent [19]

Hughes

[11] Patent Number: 5,261,411
[45] Date of Patent: Nov. 16, 1993

[54] THERMAL DRIFT CORRECTION WHILE CONTINUOUSLY MONITORING CARDIAC OUTPUT

[75] Inventor: Timothy J. Hughes, Palo Alto, Calif.

[73] Assignee: Abbott Laboratories, Abbott Park, Ill.

[21] Appl. No.: 815,345

[22] Filed: Dec. 27, 1991

[51] Int. Cl.⁵ .......................... A61B 5/02; A61B 5/00; A61B 19/00
[52] U.S. Cl. .................................. 128/668; 128/713; 128/736; 128/898
[58] Field of Search ............... 128/668, 691, 692, 713, 128/736, 642, 898

[56] References Cited

U.S. PATENT DOCUMENTS

| | | | |
|---|---|---|---|
| 3,359,974 | 12/1967 | Khalil | 128/2.05 |
| 4,236,527 | 12/1980 | Newbower et al. | 128/692 |
| 4,507,974 | 4/1985 | Yelderman | 73/861.06 |
| 4,542,748 | 9/1985 | Roy | 128/713 |
| 4,716,904 | 1/1988 | Meno | 128/713 X |
| 4,730,623 | 3/1988 | Lee | 128/692 |
| 4,745,928 | 5/1988 | Webler et al. | 128/692 |
| 4,819,655 | 4/1989 | Webler | 128/713 |
| 4,841,981 | 6/1989 | Tanabe et al. | 128/736 X |
| 4,949,724 | 8/1990 | Mahutte et al. | 128/713 |
| 4,979,514 | 12/1990 | Sekii et al. | 128/692 X |
| 4,993,420 | 2/1991 | Welkowitz | 128/691 X |
| 5,080,106 | 1/1992 | Sekii et al. | 128/691 X |
| 5,101,828 | 4/1992 | Welkowitz et al. | 128/691 X |

OTHER PUBLICATIONS

Philip, James H., et al., "Continuous Thermal Measurement of Cardiac Output," *IEEE Transactions on Biomedical Engineering*, vol. BME-31, No. 5, May 1984, pp. 393-400.

*Primary Examiner*—Randall L. Green
*Assistant Examiner*—Elizabeth Burke
*Attorney, Agent, or Firm*—Christensen, O'Connor, Johnson & Kindness

[57] ABSTRACT

A method for compensating the determination of cardiac output for a baseline blood temperature drift, or other long-term noise. The method is applicable to the continuous monitoring of cardiac output, which is carried out by modifying the temperature of blood within a heart (12) using a periodically varying electrical current that is applied to a heater (22) disposed on the outer surface of a catheter (14) inserted within the heart. A temperature sensor (24) disposed near a distal end (18) of the catheter monitors the temperature of blood leaving the heart, producing a blood temperature signal that periodically varies in a manner corresponding to the input signal. Alternatively, the temperature of blood within the heart can be modified by heat exchange with a fluid circulated within a heat exchanger (16) on the catheter, so that heat is transferred between the fluid and blood. Changes in the baseline blood temperature caused by a gradual warming of the patient from a chilled condition or due to other long term noise are compensated by either carefully selecting a measurement interval during which the blood temperature signal is filtered (by performing a discrete Fourier transform) so that the blood temperature signal (without the effect or drift) comprises only a real component, or by shifting the starting point of the input power signal to achieve the same result. The baseline temperature drift of the blood or other noise is thus in quadrature with the blood temperature signal (without drift) and has little effect on the determination of cardiac output. Further compensation in the measurement interval and/or starting time of the input signal can be made to compensate for other time delays, such as delays due to mixing volume, transport delay, and delays associated with the time constants of the apparatus used to modify the temperature of the blood and determine its temperature.

21 Claims, 9 Drawing Sheets

THERMAL DRIFT CORRECTION WHILE CONTINUOUSLY MONITORING CARDIAC OUTPUT

FIELD OF THE INVENTION

This invention generally relates to the continuous measurement of cardiac output, i.e., the volumetric rate at which blood flows through the heart, and more specifically, to a method and apparatus for correcting the cardiac output for errors due to temperature drift.

BACKGROUND OF THE INVENTION

Cardiac output, the volumetric rate at which blood is pumped through the heart, is most often determined clinically by injecting a bolus of chilled saline or glucose solution into the right auricle or right ventricle through a catheter. A thermistor disposed in the pulmonary artery is used to determine a temperature-time washout curve as the chilled injectate/blood mixture is pumped from the heart. The area under this curve provides an indication of cardiac output. Although this thermo-dilution method can give an indication of cardiac output at the time the procedure is performed, it cannot be used for continuously monitoring cardiac output. Moreover, the frequency with which the procedure is performed is limited by its adverse effects on a patient, including the dilution of the patient's blood that occurs each time the chilled fluid is injected. In addition, the procedure poses an infection hazard to medical staff from blood contact, and to the patient, from exposure to possibly contaminated injectate fluid or syringes.

Alternatively, blood in the heart can be chilled or heated in an injectateless method by a heat transfer process using a temperature-conditioned fluid that is pumped in a closed loop, toward the heart through one lumen within the catheter and back through another lumen. The principal advantages of using such a non-injectate heat transfer process to change the temperature of blood are that the blood is not diluted, and the temperature differential between the blood and the heat exchanger is much less compared to the temperature differential between an injectate fluid and blood in the typical thermo-dilution procedure.

U.S. Pat. No. 4,819,655 (Webler) discloses an injectateless method and apparatus for determining cardiac output. In Webler's preferred embodiment, a saline solution is chilled by a refrigeration system or ice bath and introduced into a catheter that has been inserted through a patient's cardiovascular system into the heart. The catheter extends through the right auricle and right ventricle and its distal end is disposed just outside the heart in the pulmonary artery. A pump forces the chilled saline solution through a closed loop fluid path defined by two lumens in the catheter, so that heat transfer occurs between the solution and blood within the heart through the walls of the catheter. A thermistor disposed at the distal end of the catheter monitors the temperature of blood leaving the heart, both before the chilled fluid is circulated through the catheter to define a baseline temperature, and after the temperature change in the blood due to heat transfer with the chilled saline solution has stabilized. Temperature sensors are also provided to monitor both the temperature of the chilled saline solution at or near the point where it enters the catheter (outside the patient's body) and the temperature of the fluid returning from the heart. In addition, the rate at which the chilled solution flows through the catheter is either measured or controlled to maintain it at a constant value. Cardiac output (CO) is then determined from the following equation:

$$CO = \frac{\dot{V}_I (\Delta T_I)}{C(\Delta T_B)} \quad (1)$$

where $\dot{V}_I$ equals the rate at which the chilled fluid is circulated through the catheter; $\Delta T_I$ equals the difference between the temperature of the chilled fluid input to the catheter and the temperature of the fluid returning from the heart; $\Delta T_B$ equals the difference between the temperature of the blood leaving the heart before the chilled fluid is circulated and the temperature of the blood leaving the heart after the chilled fluid is circulated (after the temperature stabilizes); and C is a constant dependent upon the blood and fluid properties. The patent also teaches that the fluid may instead be heated so that it transfers heat to the blood flowing through the heart rather than chilled to absorb heat from the blood.

U.S. Pat. No. 4,819,655 further teaches that the cardiac monitoring system induces temperature variations in the pulmonary artery that are related to the patient's respiratory cycle and are therefore periodic at the respiratory rate. Accordingly, Webler suggests that the signal indicative of $T_B'$ (the temperature of the chilled blood exiting the heart) should be processed through a Fourier transform to yield a period and amplitude for the respiratory cycle, the period or multiples of it then being used as the interval over which to process the data to determine cardiac output.

Instead of cooling (or heating) the blood in the heart by heat transfer with a circulating fluid, the blood can be heated with an electrical resistance heater that is disposed on a catheter inserted into the heart as taught by H. H. Khalil in U.S. Pat. No. 3,359,974. The apparatus required for this type of injectateless cardiac output measurement is significantly less complex than that required for circulating a fluid through the catheter. An electrical current is applied to the resistor through leads in the catheter, and the current is adjusted to develop sufficient power dissipation to produce a desired temperature rise signal in the blood. However, care must be taken to avoid using a high power that might damage the blood by overheating it. An adequate signal-to-noise ratio is instead preferably obtained by applying the electrical current to the heater at a frequency corresponding to that of the minimum noise generated in the circulatory system, i.e., in the range of 0.02 through 0.15 Hz. U.S. Pat. No. 4,236,527 (Newbower et al.) also describes such a system, and more importantly, describes a technique for processing the signals developed by the system to compensate for the effect of the mixing volume in the heart and cardiovascular system of a patient, even one with a relatively large heart. (Also see J. H. Philip, M. C. Long, M. D. Quinn, and R. S. Newbower, "Continuous Thermal Measurement of Cardiac Output," IEEE Transactions on Biomedical Engineering, Vol. BMI 31, No. 5, May 1984.)

Newbower et al. teaches modulating the thermal energy added to the blood at two frequencies, e.g., a fundamental frequency and its harmonic, or with a square wave signal. Preferably, the fundamental frequency equals that of the minimal noise in the cardiac system. The temperature of the blood exiting the heart is monitored, producing an output signal that is filtered at the fundamental frequency to yield conventional cardiac output information. The other modulation frequency is similarly monitored and filtered at the harmonic frequency, and is used to determine a second variable affecting the transfer function between the injection of energy into the blood and the temperature of the blood in the pulmonary artery. The data developed from the dual frequency measurements allow the absolute heart output to be determined, thereby accounting for the variability of fluid capacity of mixing volume.

Two other prior art works are relevant to the present invention. In his M.S. thesis entitled, "Electronic Augmentation of Thermo-dilution Techniques," Massachusetts Institute of Technology, Cambridge, September 1975, L. M. Rubin discloses a technique for processing thermo-dilution data wherein the assumes that the input heating signal and output blood temperature signal are exactly in phase and makes no corrections for phase shifting due to mixing volume or drift (of the baseline blood temperature). In U.S. Pat. No. 4,507,974, M. L. Yelderman applied a pseudo-random heating signal to the blood and reconstructed a dilution curve similar to that of the regular thermo-dilution technique, by cross correlating the temperature and power signals. The patient's cardiac output was then obtained by Yelderman by integrating the area under the curve, just as is done in a conventional thermo-dilution measurement.

Neither Webler, Yelderman, nor Newbower et al. teach how to minimize a potentially significant source of error that can occur during injectateless cardiac output measurements—namely the error caused by slow baseline blood temperature fluctuations. Newbower et al. does not mention the problem, and Webler's measurement of cardiac output specifically assumes that the baseline blood temperature remains constant, so that the change in the temperature of blood in the pulmonary artery is entirely due to effect of the input signal. However, the baseline blood temperature may be changing during the measurement of cardiac output, so as to cause the value for the temperature, T, of the blood leaving the heart to be in error. Such changes in the baseline temperature of the blood may be due to a long term periodic cycling of the patient's body temperature or may simply result from the patient's body warming from a chilled condition. Certain medical procedures include chilling a patient before surgery to slow metabolism, and in this instance, the change in baseline blood temperature may be attributable to a gradual warming of the patient to normal body temperature (37° C.). In either case, whether due to a long term periodic cycle or a gradual linear drift, the change in baseline blood temperature approximates a ramp wave form. This gradual variation in blood temperature can contribute a significant error to the measurement of cardiac output.

It is therefore preferable that a non-injectate method for determining cardiac output be compensated for a drift or slow fluctuations (noise) in the baseline temperature of blood entering the heart. Compensation for the effect of drift in the baseline temperature while determining cardiac output should preferably also account for a phase lag or time delay in the determination of the cardiac output, which is introduced by the mixing volume of the heart and for other time delays that arise in the measurement.

SUMMARY OF THE INVENTION

In accordance with the present invention, a method provides for compensating a cardiac output determination for a temperature drift in a baseline temperature of blood. The method includes the steps of providing a periodically varying input signal that is used for changing the temperature of blood entering a patient's heart. As a result, the temperature of the blood leaving the heart varies periodically with respect to the baseline temperature of the blood. As the blood leaves the heart, its temperature is sensed, and a blood temperature signal is produced that also varies periodically. The blood temperature signal is filtered, producing a filtered output signal having an in-phase component and a quadrature component. A measurement interval for the blood temperature signal relative to the input signal is selected, so as to insure that the filtered output signal predominantly comprises the in-phase component. The cardiac output of the heart is determined as a function of the input signal and of the filtered output signal, the effect of any baseline temperature drift being minimized in this determination because the baseline temperature drift primarily comprises the quadrature component, which is substantially out of phase with the in-phase component of the filtered output signal.

The step of selecting the measurement interval preferably comprises the step of shifting a time during which the input signal is applied relative to the measurement interval of the blood temperature signal.

Alternatively, the step of selecting the measurement interval comprises the step of shifting the measurement interval during which the blood temperature signal is filtered, so that it is at a predefined phase angle with respect to the input signal. The phase angle by which the measurement interval is shifted relative to the input signal is preferably selected as a function of a time delay (phase lag) associated with apparatus inserted into the heart to periodically vary the temperature of the blood by application of the input signal, and as a function of a time delay (phase lag) for a temperature sensor used to sense the temperature of blood leaving the heart. The phase angle by which the measurement interval is shifted relative to the input signal is selected further as a function of a time delay (phase lag) associated with a mixing volume of the heart. The phase lag of the mixing volume is determined by averaging the filtered output signal over a plurality of measurement intervals, and the angle by which the measurement interval is shifted in phase is chosen to make the phase angle of the average filtered output signal substantially equal to zero. As an alternative method to determine the phase lag of the mixing volume, a spectral analysis of the filtered output signal is performed over a plurality of measurement intervals to determine a phase angle for the filtered output signal in a frequency domain. This phase angle is then adjusted to equal zero by suitable selection of the measurement interval.

The foregoing aspects and many of the attendant advantages of this invention will become more readily appreciated by reference to the following detailed description, when taken in conjunction with the accompanying drawing.

DETAILED DESCRIPTION OF THE PREFERRED EMBODIMENT

Figure 1:
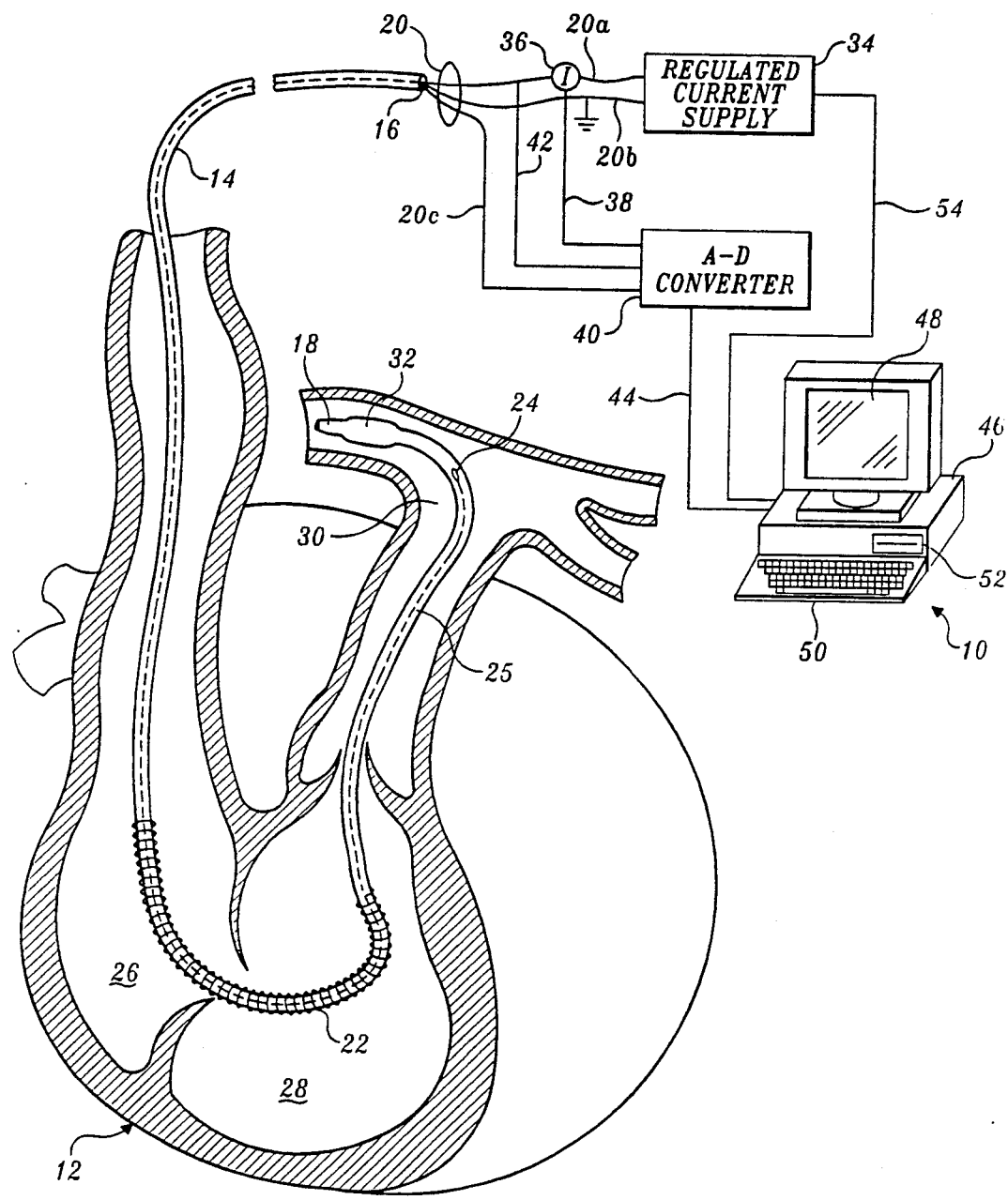
FIG. 1 is a block diagram of a first embodiment of a system for measuring cardiac output in which the present invention is applied to compensate for long term temperature drift and other noise.

A first embodiment of a cardiac output monitoring system that incorporates the present invention to compensate for blood temperature drift is shown generally in FIG. 1 at reference numeral 10. A human heart 12 is schematically illustrated in this figure, with a portion of the heart cut away to show the disposition of a catheter 14 that is inserted into heart 12 through a patient's cardiovascular system. Catheter 14 has a proximal end 16 and a distal end 18. A plurality of leads 20 extend longitudinally through catheter 14 (within lumens that are not separately shown) and include leads 20a and 20b that carry an electrical current to an electrical resistance heater 22. In the preferred form of this system, heater 22 comprises a coil of insulated copper, stainless steel, nickel, or nichrome wire approximately 12 cm in length that is wound around catheter 14 approximately 10 to 15 cm from distal end 18. Heater 22 has a nominal resistance of from 15 to 30 ohms. Leads 20c are connected to a temperature sensor 24, which is spaced apart from distal end 18 and generally mounted on the external surface of the catheter so that it can readily sense the temperature of blood flowing past the distal end as the blood is pumped from heart 12.

As shown clearly in FIG. 1, catheter 14 extends through a right auricle 26, a right ventricle 28, and into a pulmonary artery 30 of the patient whose cardiac output is being monitored. Adjacent distal end 18 is disposed a balloon 32, which is inflated to float distal end 18 upwardly from right ventricle 28 into pulmonary artery 30. Heater 22 can be positioned entirely within right auricle 26, or as shown, may extend from right auricle 26 into right ventricle 28.

A regulated current supply 34 supplies a periodic electrical current used to sinusoidally generate heat at heater 22, at a voltage ranging from 10 to 25 volts peak amplitude. Alternatively, the current supply can provide a direct current that is cycled on and off, producing a square wave. As the current flows through the wire coil comprising heater 22, it produces heat in proportion to the $I^2R$ losses in the heater (where I is the current, and R is the resistance of the heater). The heat produced is transferred to the blood within right auricle 26 and right ventricle 28. A current sensor 36 produces a signal indicative of the magnitude of the electrical current flowing through lead 20a to heater 22, and this signal is input through leads 38 to analog-to-digital (A-D) converters 40. A second input to A-D converters 40 is a voltage signal that indicates the voltage developed across heater 22; this voltage signal is conveyed by a lead 42. The third input to the A-D converters comprises the signal produced by temperature sensor 24, which is indicative of the temperature of the blood leaving heart 12. Temperature sensor 24 is connected to leads 25 that comprise the distal end of leads 20c. Digitized signals from A-D converters 40 are conveyed through leads 44 to input ports (not separately shown) on a portable computer 46.

Associated with portable computer 46 is a video display 48 on which data defining the cardiac output of heart 12 are displayed, along with other data and information. A keyboard 50 is connected to portable computer 46 to provide for user input and control of the cardiac output measurement. In addition, portable computer 46 includes a hard drive or floppy drive 52 that is used for magnetic storage of data, test results, and programs such as the software controlling the measurement of cardiac output. Portable computer 46 controls regulated current supply 34 by supplying control signals transmitted through leads 54 that extend between the regulated current supply and the portable computer.

The electrical current that energizes heater 22 to heat the blood flowing through heart 12 is supplied either in the form of a sine wave having a 30-to 60-second period, or as a square wave with an energized period ranging between 15 and 30 seconds (followed by a like duration during which no current is supplied). The power developed by heater 22 thus represents a periodic input signal, whereas the signal developed by temperature sensor 24 comprises an output signal indicative of the temperature of the blood leaving the heart. To determine power dissipated within heater 22, the digitized signals indicative of the current flowing through the heater and voltage drop across it are multiplied together by portable computer 46. The power dissipated within heater 22 to heat the blood flowing through heart 12, i.e., the peak to peak amplitude, is therefore easily determined and is defined as the "input signal" for purposes of the following discussion. Accordingly, the power applied, which represents the input signal, and the temperature of the blood exiting the heart through the pulmonary artery, which represents the output (or blood temperature) signal, are used to determine the cardiac output of heart 12, for example, by determining the solution to the following equation:

$$CO = \frac{|P(\omega)| * Cb}{|\Delta T(\omega)|} \quad (2)$$

where CO is the cardiac output; $|P(\omega)|$ is the magnitude of the heating power developed by the electrical current flowing through heater 22; $|\Delta T(\omega)|$ is the corresponding magnitude of the change in blood temperature (i.e., the output signal); $\omega$ is the angular frequency in radians per second of the input signal and the blood temperature signal; and Cb is the product of a specific heat and density of blood.

Figure 2:
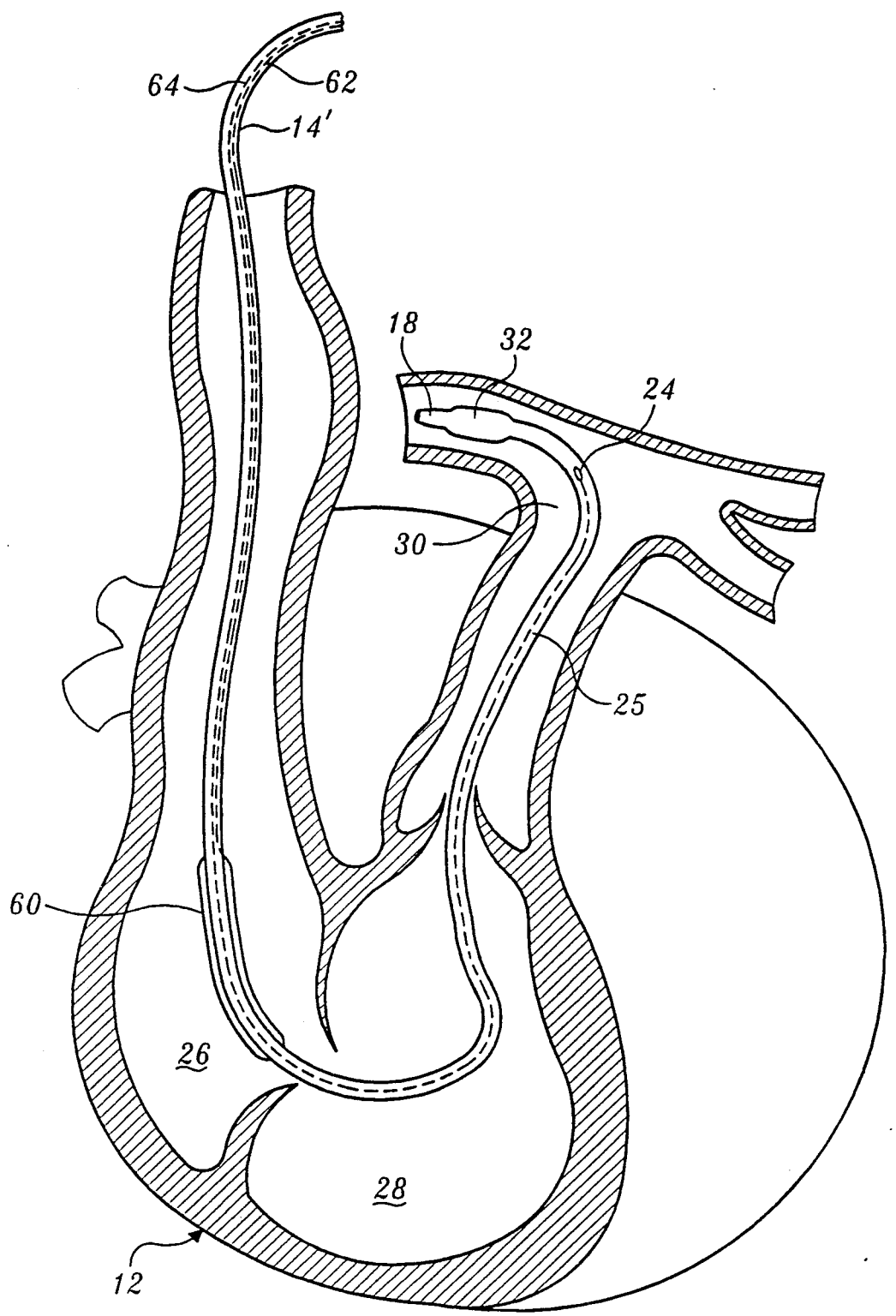
FIG. 2 is a cut-away view of a human heart, showing the disposition of a catheter through which a temperature-conditioned fluid is circulated to change the temperature of the blood within the heart.

An alternative technique for developing an input signal and an output signal that can be used to determine the cardiac output of heart 12 is shown in FIG. 2. In this method, a catheter 14' is used to convey a cooling or heating fluid to a heat exchanger 60 formed on the catheter, set back from its distal end so that the heat exchanger is within right auricle 26. Two lumens (not separately shown) within catheter 14' define a supply fluid path 62 through which a liquid cooled to a temperature well below that of the body temperature of the patient is conveyed to heat exchanger 60, and a return fluid path 64 through which the fluid flows back to a source of the fluid, external to the patient's body. In most other aspects of its configuration and use, catheter 14' is similar to catheter 14, shown in FIG. 1. Like catheter 14, catheter 14' includes temperature sensor 24 disposed adjacent its distal end 18 so that it is positioned within pulmonary artery 30.

Instead of cooling a fluid to a temperature lower than the temperature of blood entering heart 12 through catheter 14', the fluid may be heated above the temperature of the blood so that it transfers heat to the blood, just as heater 22 does. In either case, whether the input signal cools the blood or heats it, the cardiac output measurment system changes the temperature of blood in the heart on a periodic basis so that the output signal produced by temperature sensor 24 changes periodically in response thereto. Furthermore, regardless of the method used to transfer heat to the blood within the heart, the change in the temperature of blood flowing from the heart, i.e., the output signal, is delayed or phase shifted relative to the input signal due to the time required to change the temperature of the mass of blood within the right auricle and right ventricle. The effect of the mass of blood within the heart on the relative time or phase angle between changes in the input signal and corresponding changes of the blood temperature signal is referred to as the mixing volume delay. The mixing volume delay increases with volume and varies inversely with cardiac output.

In addition to the mixing volume delay, the phase of the output signal differs from that of the input signal due to a transport delay, which is a function of the rate at which blood heated by heater 22 or by heat exchanger 60 that has mixed with the other blood in the heart reaches temperature sensor 24. There is also a delay that is a function of the time constant of the catheter/heater (or heat exchanger), and a delay caused by the time constant of temperature sensor 24. Commonly assigned copending U.S. patent application, Ser. No. 07/815,068, filed Dec. 27, 1991, entitled, Apparatus And Method For Continuously Monitoring Cardiac Output, now U.S. Pat. No. 5,217,019, describes a method for determing cardiac output based on phase angle between the input and output signals. The effect of the changes in relative phase angle between the input signal and the output signal due to transport delay, mixing volume, the time constants of the catheter and other portions of the measurement system are readily compensated, as explained therein.

COMPENSATION FOR BASE LINE TEMPERATURE DRIFT AND OTHER NOISE

Figure 3:
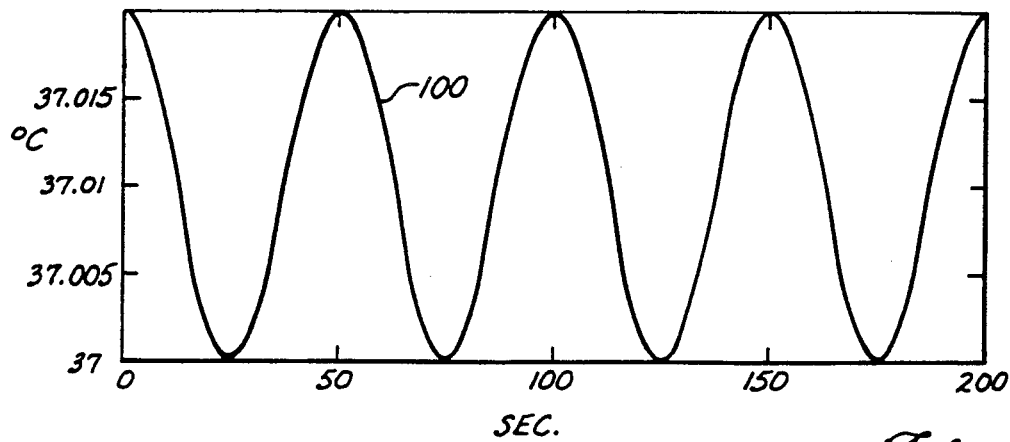
FIG. 3 is a graph showing a periodically varying blood temperature signal over time, for an ideal case in which there is no change in baseline blood temperature due to drift or other noise.

In an ideal case, any change in the temperature of the blood leaving heart 12 that is measured by temperature sensor 24 within pulmonary artery 30 would be caused only by the periodic transfer of heat from heater 22 (shown in FIG. 1) or the transfer of heat between heat exchanger 60 (shown in FIG. 2) and the blood within the heart. In this ideal case, as shown in FIG. 3, the blood temperature signal would represent a pure sinusoidal wave corresponding to the sinusoidal input signal used to change the temperature of the blood. Thus, if the input signal used to change the temperature of blood within the heart has a period of 50 seconds during which heat is transferred into the blood from the heater, the blood temperature signal would be sinusoidal, with a minimum value at the patient's body temperature (normally 37° C.) and a maximum value, for example, of 37.02° C. A wave form 100 illustrative the ideal case is shown in FIG. 3. Four cycles of wave form 100 extend over a total time interval of 200 seconds.

Figure 4:
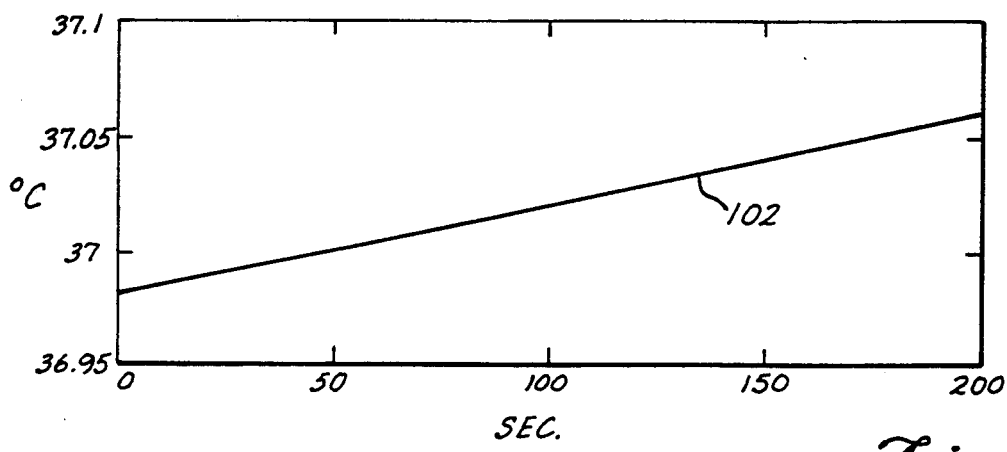
FIG. 4 is a graph showing drift in a patient's baseline blood temperature over time.
Figure 5:
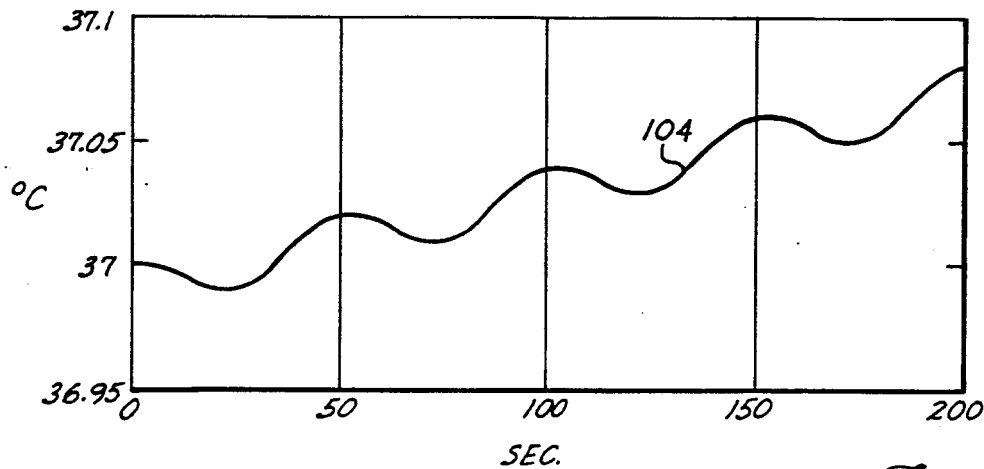
FIG. 5 is a graph showing the periodically varying blood temperature signal superimposed on the long term drift of the baseline blood temperature.

Unfortunately, however, a patient's baseline blood temperature is often not stable at 37° C., but instead either slowly cycles over a time much longer than the period of one cycle of the input signal, or increases gradually from a chilled state. In any event, such a slow change in baseline blood temperature can be approximated by a wave form 102, which increases linearly generally as shown in FIG. 4. Wave form 102 increases from a temperature of approximately 36.98° C. to a temperature of about 37.06° C. during the same 200 second time interval shown for the blood temperature signal in FIG. 3. If subjected to such a drift in the baseline temperature, the temperature of blood leaving the heart, i.e., the temperature of blood within the pulmonary artery will appear as a periodically varying wave form superimposed on a ramp wave, as represented in FIG. 5 by a wave form 104.

It should be clear that cycle-to-cycle changes in the blood temperature signal caused by such gradual changes in the baseline blood temperature, i.e., changes due to long-term temperature drift or noise having a relatively long period, can cause a significant error in the determination of cardiac output, since the determination of cardiac output is based upon both the changes in blood temperature within the pulmonary artery and the power input to change the blood temperature.

Figure 6A:
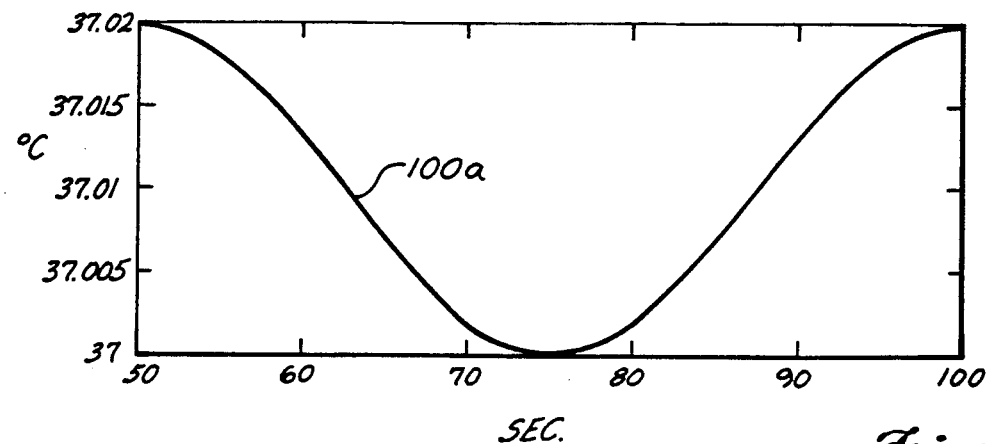
FIG. 6A is a graph illustrating a blood temperature signal over a predefined measurement interval that is selected to yield substantially only a real component of the discrete Fourier transform of the blood temperature signal.

FIG. 6A illustrates a wave form 100a that comprises a single cycle of the blood temperature signal for the ideal case where the cycle corresponds to a measurement interval of the blood temperature signal that extends from 50-100 seconds of wave form 100. The measurement interval is carefully selected so that it starts when wave form 100a is at its peak value and thus represents one cycle of a cosine function.

Figure 6B:
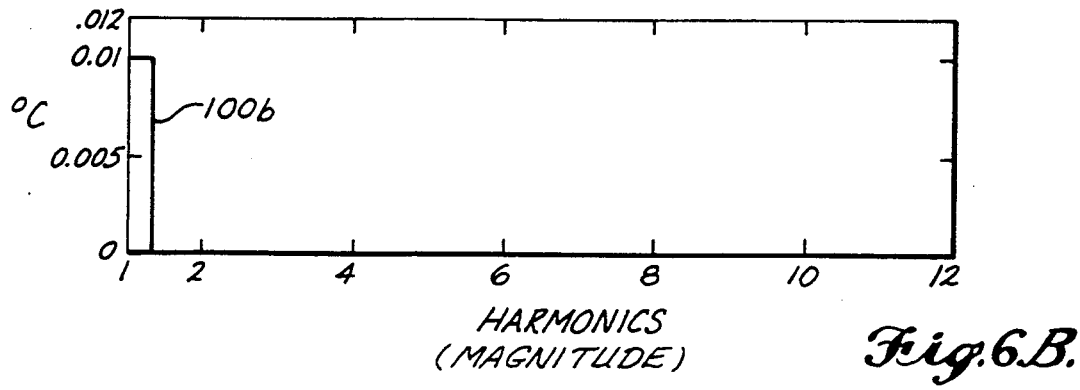
FIG. 6B is a graph showing the magnitude of a fundamental and its harmonics resulting from a discrete Fourier transform of the blood temperature signal of FIG. 6A.
Figure 6C:
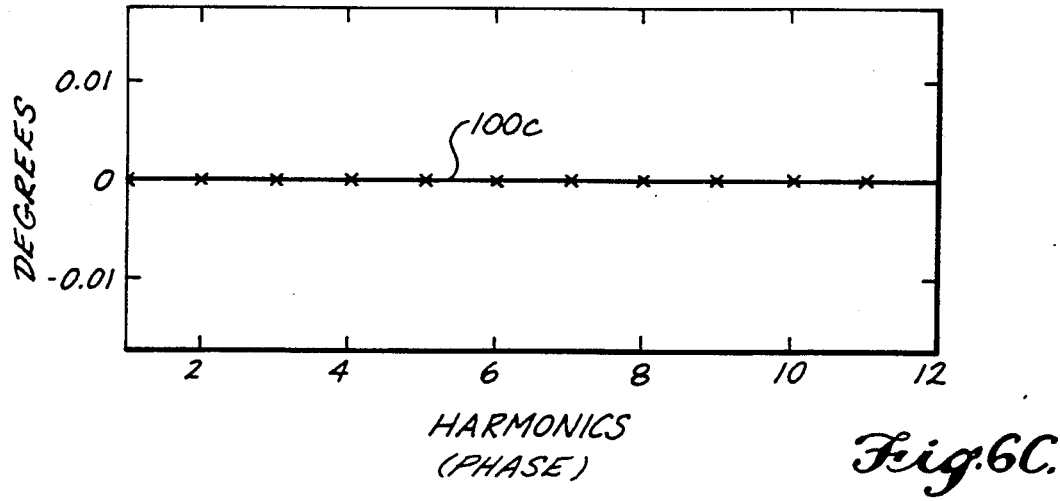
FIG. 6C is a graph of phase resulting from the discrete Fourier transform of the blood temperature signal of FIG. 6A.

If the blood temperature signal represented by wave form 100a is digitized by A-D converter 40 and the resulting digital signal is digitally filtered by portable computer 46, for example, by performing a discrete Fourier transform, both a magnitude and a phase for the signal are obtained for the fundamental and each of the harmonics of the 0.02 Hz blood temperature signal wave form 100a. Since wave form 100a comprises a pure sinusoidal signal, virtually all of its energy resides in the fundamental, as shown in FIG. 6B. In the ideal case, where there is no long term noise or baseline temperature drift affecting the signal, selection of the measurement interval so that wave form 100a corresponds to a cosine function ensures that the phase angle determined by the discrete Fourier transform is 0° for the fundamental (and all harmonics) of the signal, as shown in FIG. 6C. Virtually all of the energy in a complex representation of wave form 100a thus resides in its real component, with none of the energy in its imaginary component.

Figure 7A:
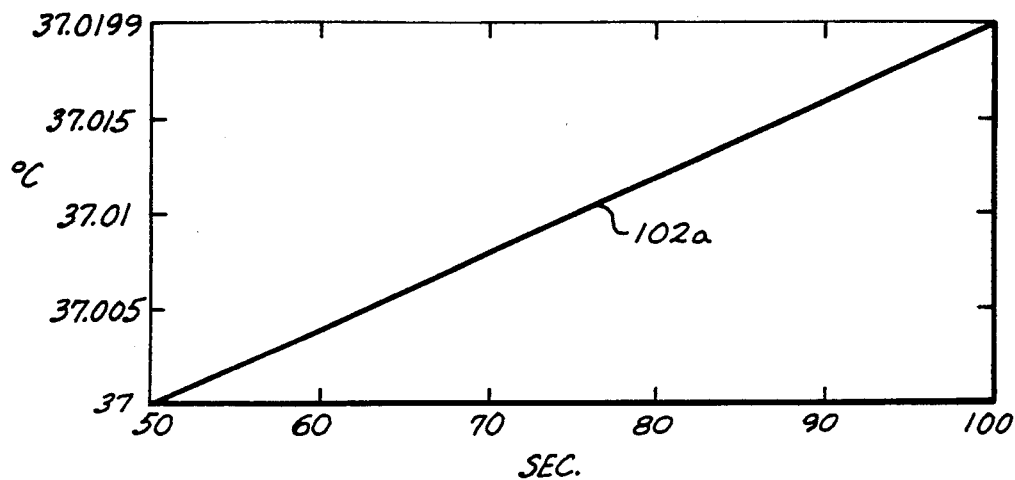
FIG. 7A is a graph of temperature drift over the predefined measurement interval of FIG. 6A.
Figure 7B:
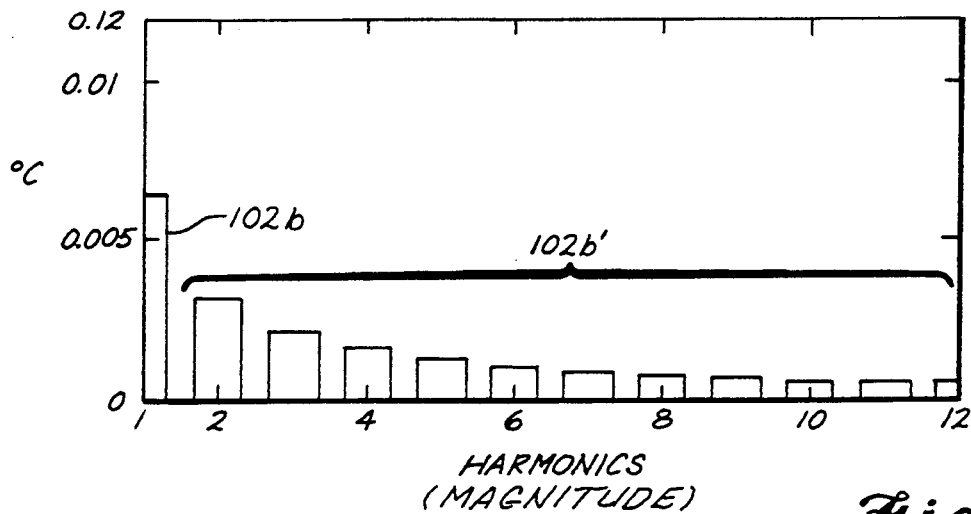
FIG. 7B is a graph of the magnitudes resulting from the discrete Fourier transform of baseline blood temperature drift in FIG. 7A.
Figure 7C:
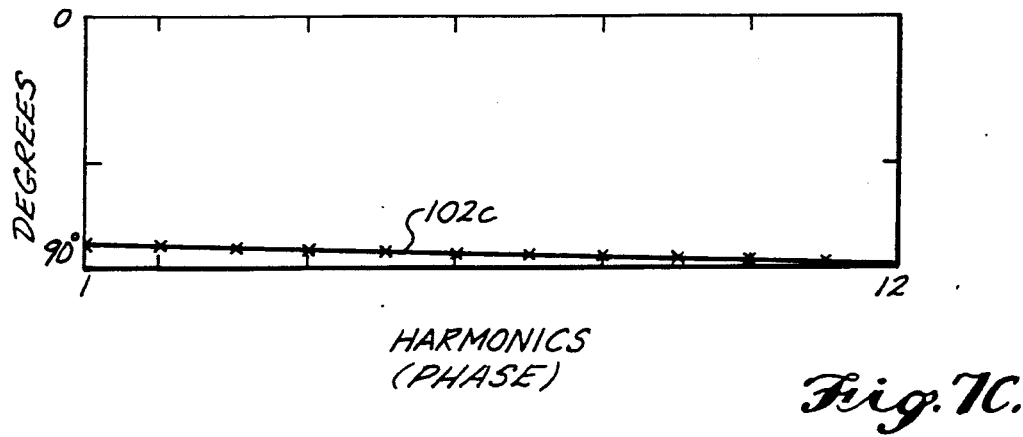
FIG. 7C is a graph of phase resulting from the discrete Fourier transform of the baseline blood temperature drift in FIG. 7A.

Referring now to FIG. 7A, the same measurement interval from 50-100 seconds is applied to wave form 102, producing a wave form 102a that starts at about 37° C. and rises linearly to approximately 37.02° C. After this signal has been digitized by A-D converter 40, it is digitally filtered by applying a discrete Fourier transform, yielding values for the magnitude and phase of the signal as shown in FIGS. 7B and 7C. The magnitude of the fundamental (0.02 Hz), represented by bar graph 102b, is approximately 0.0065° C., and the remaining harmonics represented by bars 102b' are correspondingly lower. As shown in FIG. 7C, the phase of the fundamental and of each of the harmonics is approximately equal to $-90°$C. Thus, the energy of wave form 102a is generally in quadrature relationship with that of wave form 100a when determined over the selected measurement interval, as shown in FIGS. 6A through 6C.

Figure 8A:
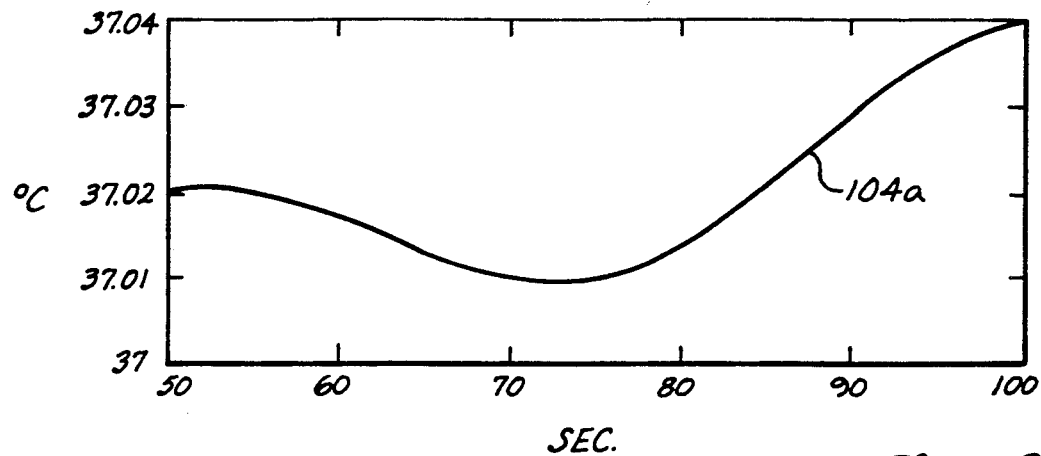
FIG. 8A is a graph of the blood temperature signal as affected by temperature drift over the predefined measurement interval.
Figure 8B:
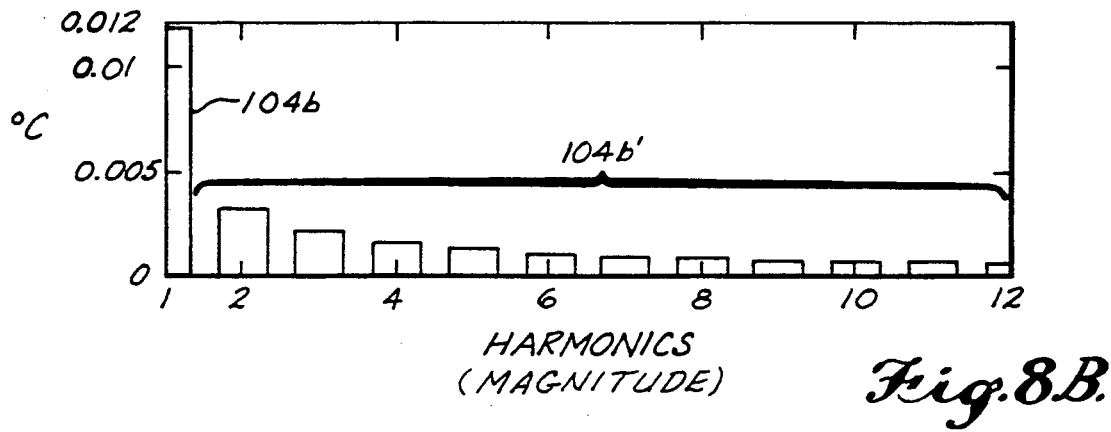
FIG. 8B is a graph of the magnitude for the fundamental and its harmonics that results from the discrete Fourier transform of the blood temperature signal affected by temperature drift, as shown in FIG. 8A.
Figure 8C:
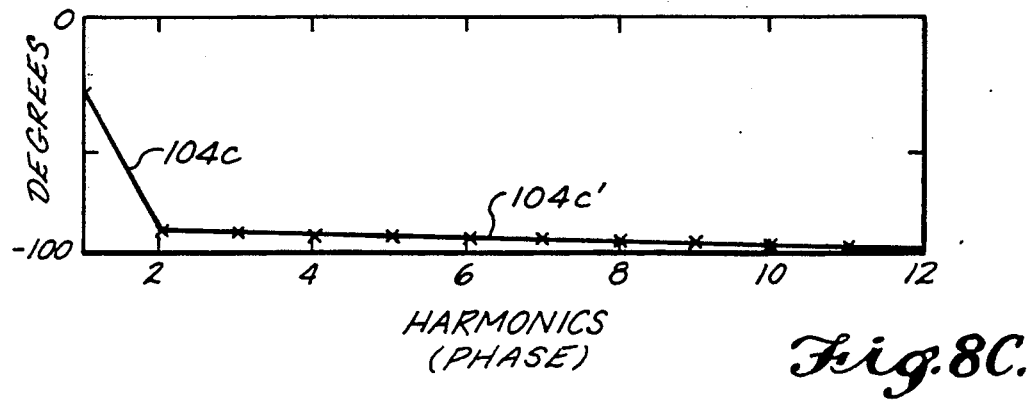
FIG. 8C is a graph of phase for the discrete Fourier transform of the blood temperature signal affected by temperature drift, as shown in FIG. 8A.

In FIG. 8A, the same measurement interval is applied to a wave form 104a, which represents the sinusoidal variation in blood temperature signal of wave form 100, superimposed on wave form 102. Again, by carefully selecting the measurement interval so that it corresponds to a cosine function, i.e., so the blood temperature signal (without drift) comprises the real component of the complex representation of wave form 104a, the effect of the drift of baseline temperature is substantially reduced since the contribution of the baseline temperature drift is in quadrature relationship with the periodically varying blood temperature signal (without drift). Wave form 104a in FIG. 8A is digitized by A-D converter 40, and digitally filtered through a discrete Fourier transform, producing magnitudes for the fundamental represented by a bar 104b and for each of the harmonics, as represented by bars 104b' (shown in FIG. 8B). The magnitude of the fundamental, bar 104b, is approximately 0.0118° C., only 18% greater than the corresponding value for the ideal case of the pure sinusoidal wave form 100a (without drift), which has a zero-to-peak magnitude of 0.01° C. The 18% error due to the contribution of baseline drift can be reduced to almost zero, if it is known that the phase angle of the blood temperature signal (without drift) that is to be measured is exactly zero with respect to the selected measurement interval, by using only the real (or in phase) portion of the blood temperature signal magnitude. If an initial selection of the measurement interval does not yield a corresponding complex blood temperature signal value that comprises only a real component when filtered with a discrete Fourier transform, the measurement interval can be shifted so that during successive determinations of the magnitude of the blood temperature signal, the contribution of baseline temperature drift or other long term noise is negligible.

Figure 9A:
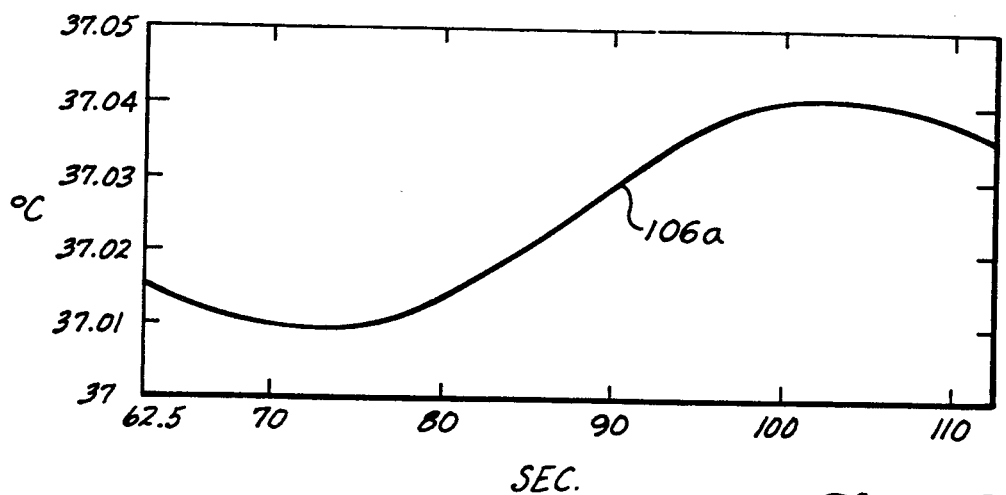
FIG. 9A is a graph of the blood temperature signal as affected by temperature drift, illustrating a worst case selection of a measurement interval.
Figure 9B:
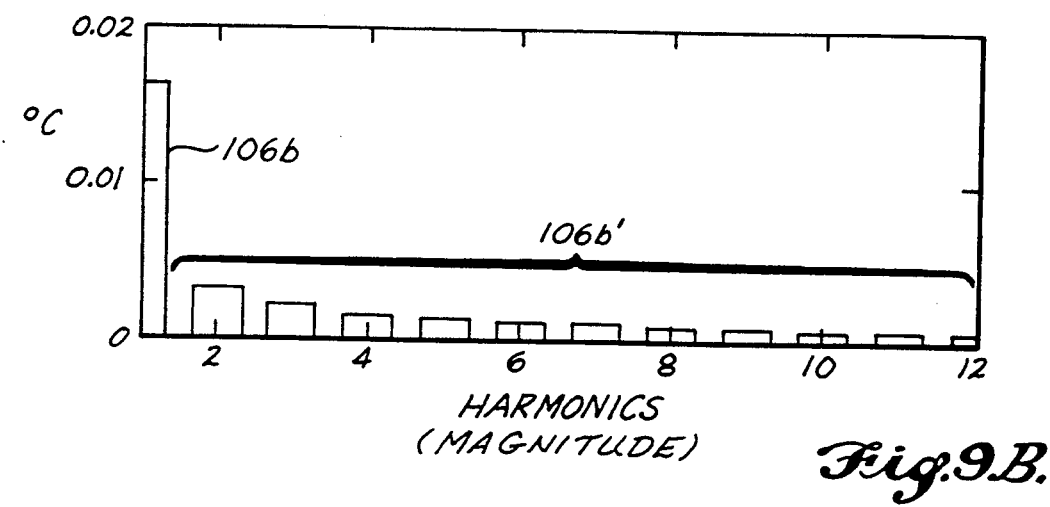
FIG. 9B is a graph of magnitude resulting from the discrete Fourier transform of the blood temperature signal affected by temperature drift, as shown in FIG. 9A.
Figure 9C:
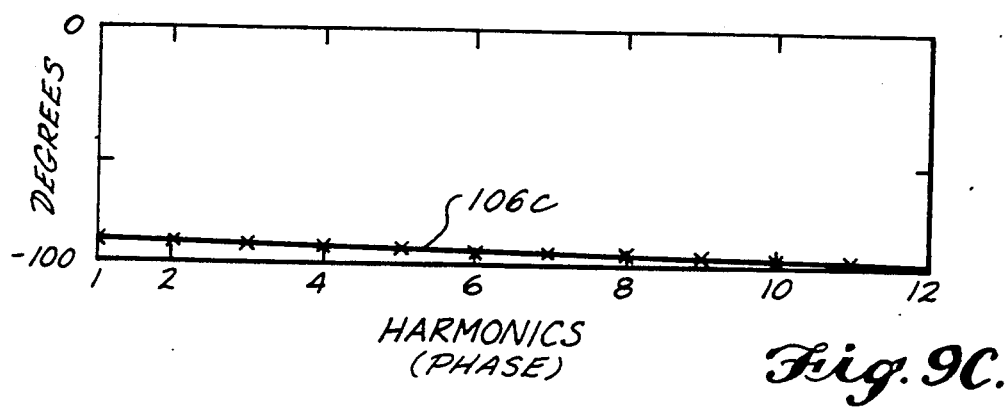
FIG. 9C is a graph of phase resulting from the discrete Fourier transform of the blood temperature signal affected by temperature drift, as shown in FIG. 9A.

FIGS. 9A through 9C illustrate a worst case selection of the measurement interval, wherein the contribution of the input signal to the blood temperature and the baseline temperature drift add to each other in phase. In this example, the measurement interval is selected to start at 62.5 seconds and to conclude at approximately 112.5 seconds; the magnitude of the fundamental, represented by a bar 106b, is approximately equal to 0.0164° C. (The magnitude of the higher harmonics, represented by bars 106b' can generally be ignored if only the first harmonic, i.e., the fundamental, is being used.) The phase angle of wave form 106a associated with the inappropriately selected measurement interval shown in FIG. 9A is approximately $-90°$ for the fundamental and each of the harmonics. Thus, the blood temperature signal has only an imaginary component in the discrete Fourier transform, which adds linearly in phase with the baseline temperature drift component instead of in quadrature, producing an error of approximately 64%. The selection of a measurement interval as shown in FIG. 9A thus represents a worst case condition, since the blood temperature signal (without drift) and the baseline temperature drift add together to produce a maximum error.

Figure 10A:
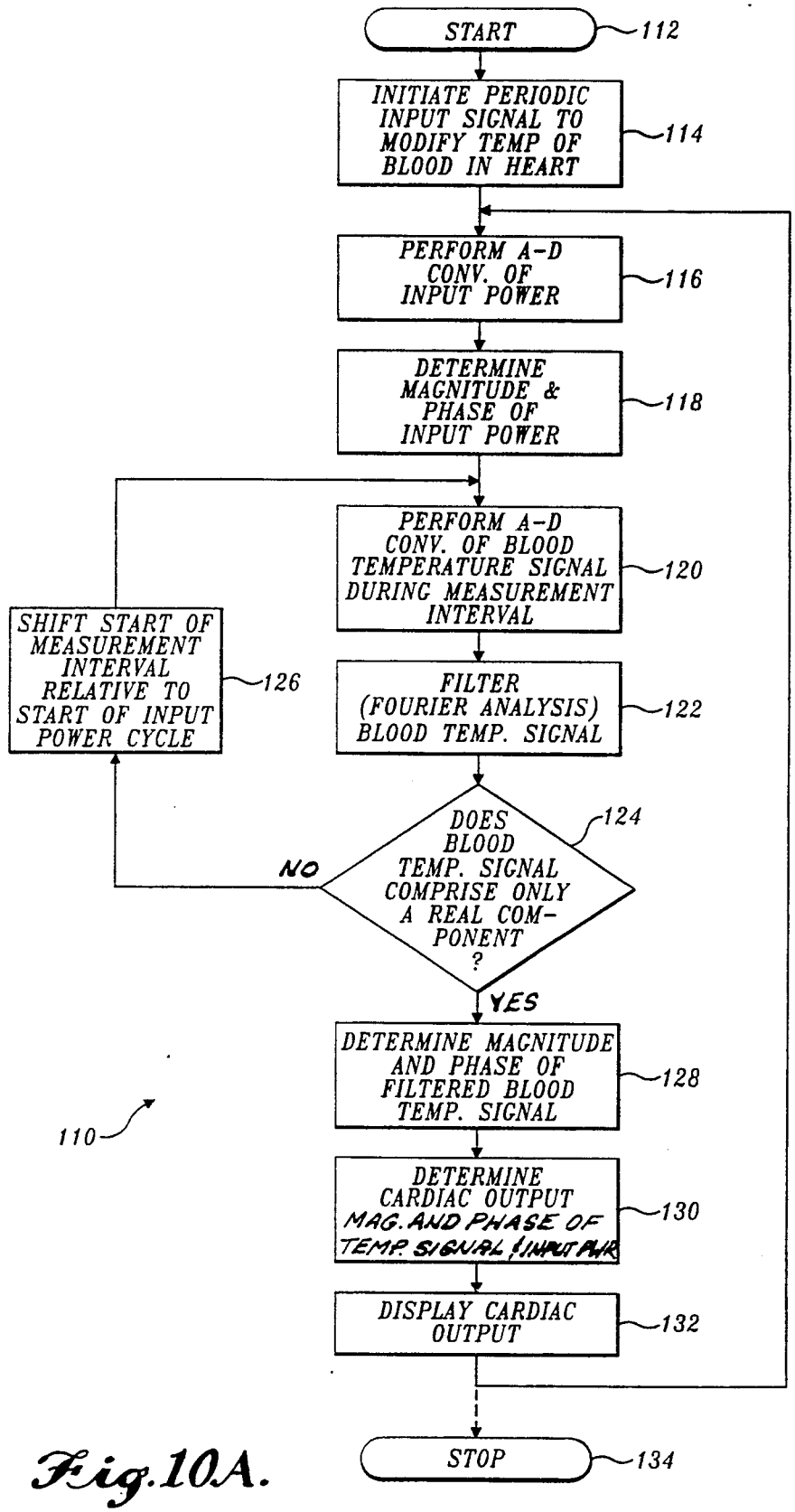
FIG. 10A is a flow chart illustrating the logical steps carried out in determining the cardiac output compensated for baseline temperature drift and other noise.

The method used to compensate cardiac output for baseline temperature drift or other long term noise is illustrated in a flowchart 110 in FIG. 10A. This method makes use of the phasal relationship between the measurement interval and the input signal. The technique used to minimize the errors caused by changes in the baseline blood temperature is applicable to several different methods for determining cardiac output, as will be evident from the following discussion.

Flowchart 110 begins at a start block 112 and proceeds to a block 114 wherein a periodic input signal is initiated to modify the temperature of blood in heart 12 (FIG. 1). As noted above, the periodic input signal can comprise a periodically varying electrical current with a period of 30-60 seconds, which is used to produce heat due to the resistance of heater 22, or may comprise the flow of a heat transfer fluid through heat exchanger 60 (FIG. 2) which is periodically started and stopped, for example, flowing for 25 seconds, followed by 25 seconds during which the fluid flow is interrupted. Likewise, the electrical current that applies power to heater 22 can be a square wave with an on-time of 15-30 seconds, instead of a sinusoidal wave form. In a block 116, the power applied to change the temperature of blood within heart 12, which represents an input signal, is digitized by A-D converter 40, producing a corresponding digitized input power signal that is processed by portable computer 46. The input signal can be processed during one or an integer number of cycles of the input signal (at the frequency $\omega$ radians/second). As indicated in a block 118, portable computer 46 determines a magnitude and phase for the input power as a function of the digitized input power signal.

In a block 120, the blood temperature signal developed by temperature sensor 24 is digitized by A-D converter 40, producing a digitized blood temperature signal that is processed by portable computer 46 during a selected measurement interval (during one or an integer number of cycles). The measurement interval initially selected is a best guess that can be determined from the phase of the input power and empirical data concerning the size of heart 12 and other physical parameters that are likely to affect the relative time (or phase) between application of the input power signal and measurement of the blood temperature signal. The digitized blood temperature signal is filtered in a block 122, preferably by applying a discrete Fourier transform, to determine a magnitude and phase angle for the fundamental of the blood temperature signal, thereby determining its real and imaginary components. A decision block 124 determines if the blood temperature signal comprises only a real component, i.e., whether the baseline temperature drift or other noise is in quadrature relationship with the blood temperature signal (without drift). If not, a block 126 shifts the start of the measurement interval relative to the start of the input power cycle.

It should be apparent that the blood temperature signal comprises a plurality of cycles, and that the measurement interval selected can start at any time during a cycle of the blood temperature signal and is substantially equal in duration to the period of each cycle (or an integer number of such cycles). Accordingly, the start of the measurement interval initially selected can be arbitrary, enabling the desired quadrature relationship between the blood temperature signal (without drift) and the baseline blood temperature drift (or other long term noise) to be achieved by shifting the relative phase (or starting point) of the input signal that is used to change the temperature of blood within heart 12. Any relative change in phase (starting point) between the input power signal and the measurement interval can be achieved by shifting one or both of these two parameters relative to the other to achieve the desired quadrature relationship so that the blood temperature signal (without drift) comprises only a real component of the complex representation of the blood temperature signal (with drift). After block 126, the logic returns to block 120 to repeat the cycle.

Once an affirmative result is obtained from decision block 124, the program logic proceeds with a block 128 wherein the magnitude and phase of the filtered blood temperature signal are determined. As a consequence of performing a discrete Fourier transform of the blood temperature signal, the magnitude and phase angle of the blood temperature signal are determined by portable computer 46. These values, along with the magnitude and phase angle of the input power determined in block 118 are then used to determine the cardiac output, as indicated in a block 130. Since several different techniques can be used for determining the cardiac output as a function of these parameters, the details of the determination are discussed below, with reference to FIG. 10B. After cardiac output is determined in block 130 (compensated for the baseline temperature drift, and any other long-term noise) portable computer 46 displays the cardiac output value on video display 48 (FIG. 1). The cardiac output thus determined may also include compensation for time delays resulting from certain physical aspects of the catheter and other apparatus used during the determination and delays resulting from the mixing volume within heart 12 and the time required for blood that has been changed in temperature by the input signal to reach temperature sensor 24. Compensation of the cardiac output for these other factors is explained below.

Figure 10B:
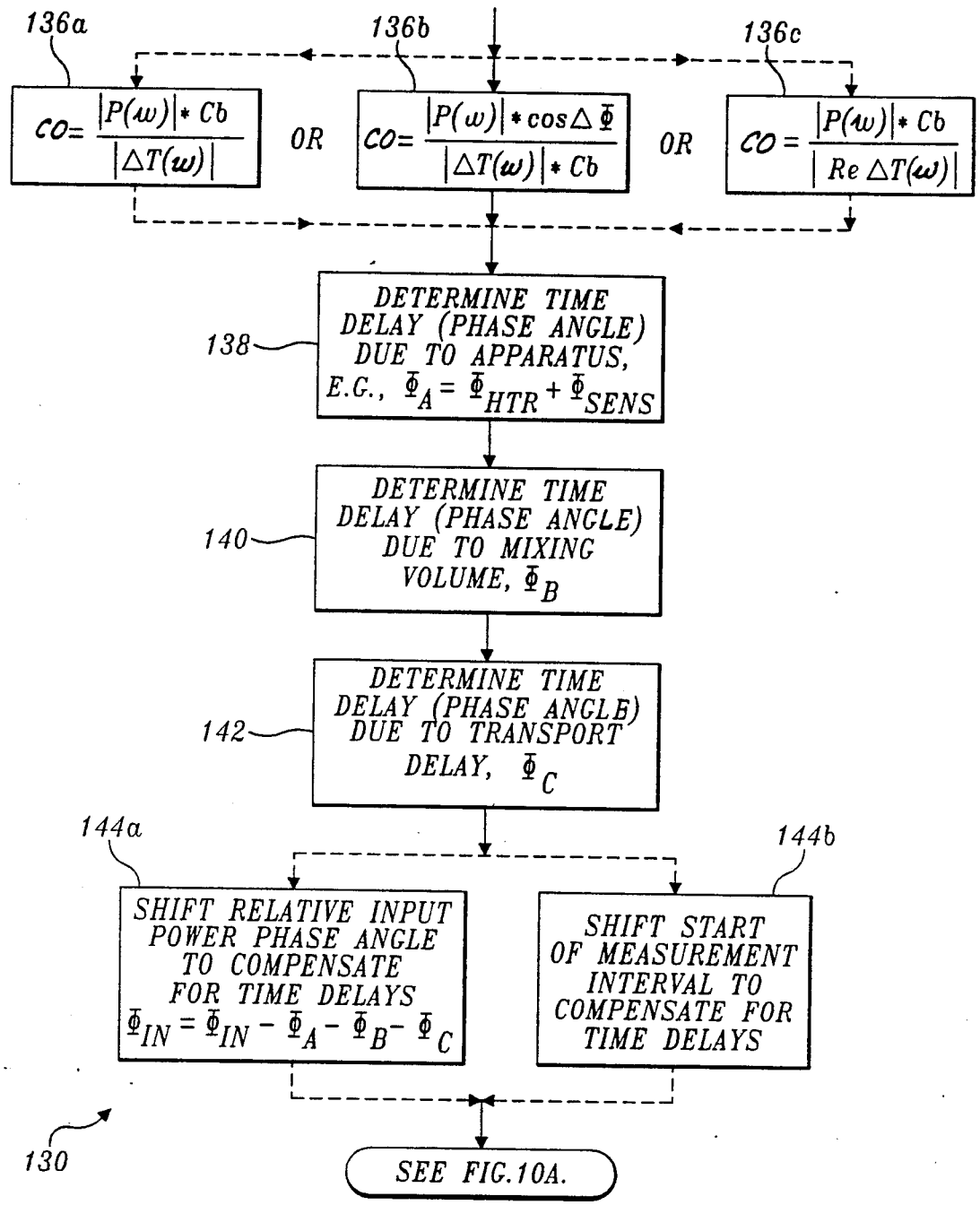
FIG. 10B is a flow chart illustrating different techniques for determining the cardiac output and adjusting cardiac output to compensate time delays (or relative phase angle errors) caused by time delays associated with the apparatus used to change the temperature in the heart and delays due to mixing volume and transport of the blood through the heart.

Referring to FIG. 10B, details of block 130 are shown to explain more clearly how the cardiac output is determined and compensated for the various time delays noted above. Cardiac output can be determined as a function of input power magnitude, blood temperature signal, and Cb, the product of the specific heat of blood and its density. The three different expressions that can be used to determine cardiac output are represented in blocks 136a, 136b, and 136c. In block 136a, cardiac output is determined according to the conventional equation:

$$CO = \frac{|P(\omega)| * Cb}{|\Delta T(\omega)|} \quad (3)$$

wherein $P(\omega)$ is the input power at frequency $\omega$ (radians/second), $\Delta T(\omega)$ is the blood temperature signal at frequency $\omega$, and Cb is the product of the specific heat of blood and its density.

Alternatively, cardiac output can be determined from the expression:

$$CO = \frac{|P(\omega)| * \cos\Delta\Phi}{|\Delta T(\omega)| * Cb} \quad (4)$$

wherein the same parameters are used as in block 136a and a phase angle between the input power signal and the blood temperature signal represented by $\Delta\Phi$ is used to more accurately determine cardiac output. The technique referenced by the expression in block 136b is disclosed in the copending, commonly assigned patent application cited above.

Finally, a block 136c shows yet another alternative expression for determining cardiac output as follows:

$$CO = \frac{|P(\omega)| * Cb}{|Re\Delta T(\omega)|} \quad (5)$$

In the above Equation 5, only the real part of the blood temperature signal is used (represented by $Re\Delta T(\omega)$), and it is assumed that an ideal measurement interval has been selected. The real part of the blood temperature signal is equal to its magnitude multiplied by the cosine of its phase angle, both of which are determined by taking the discrete Fourier transform of the blood temperature signal.

Using any one of the three techniques for determining cardiac output defined in blocks 136a through 136c, a value is determined that can then be compensated for several different time delays. It should be apparent that the compensation for such delays is optional, and may be ignored under certain situations, for example, if the flow rate through the heart is relatively high.

In a block 138, a time delay due to the time constant of apparatus used in changing the temperature of the blood in the heart and for monitoring the blood temperature as it leaves the heart is determined. In essence, a time delay is equivalent to a phase angle relative to the input signal, which affects the time at which the blood temperature signal changes in response to the input signal. For example, a time constant $TC_{HTR}$ for the heater can be empirically determined and the corresponding phase shift due to the heater $\Phi_{HTR}$ can be determined from the following expression:

$$\Phi_{HTR} = -ARCTAN(\omega TC_{HTR}) \tag{6}$$

Based on this determination, an equivalent heater time delay $TD_{HTR}$ (using the period of the input signal) is defined by:

$$TD_{HTR} = \Phi_{HTR} * \text{Period}/2\pi \tag{7}$$

Similarly, a time delay and phase shift due to the time constant of the temperature sensor can be determined. The total phase shift due to the heater and sensor is represented by $\Phi_A$.

In a block 140, a time delay (or corresponding phase angle) due to the mixing volume of heart 12 is determined. The phase angle is represented by $\Phi_B$. In a block 142, the time delay and corresponding phase angle due to the transport delay, i.e., the time required for blood having a temperature modified by the input power signal to reach the temperature sensor. The time delay associated with the mixing volume in block 140 and the time delay due to transport determined in block 142 can either be estimated based upon knowledge of the patient's heart, or can be determined through other techniques. Specifically, the phase lag due to the mixing volume can be determined by performing a spectral analysis of the blood temperature signal over a plurality of measurement intervals to determine a phase angle for the signal in the frequency domain. Alternatively, the phase lag caused by the mixing volume can be determined by averaging the phase angle of the blood temperature signal (determined by the discrete Fourier transform), over a plurality of measurement intervals. The angle by which the measurement interval is shifted in phase relative to its prior position is chosen as necessary to make the average phase angle of the blood temperature signal substantially equal to zero. Averaging the phase angle in this manner works best when the baseline blood temperature is fluctuating gradually up and down, rather than changing in a unidirectional drift.

Another approach used to determine the compensation required for mixing volume is as follows. Cardiac output is initially determined based, for example, on the magnitude of the input power, its phase, the magnitude of the blood temperature signal and its phase, but without correcting for the mixing volume phase delay. An estimate for mixing volume phase angle is made by subtracting the phase contribution of the apparatus (i.e., the heater, and temperature sensor), and the transport delay from the total phase error. Using the approximate value for cardiac output and estimated value for the mixing volume phase angle, $\Phi_B'$, the mixing volume, $V_{mix}$, is determined from the following equation:

$$V_{mix} = CO * TAN(\Phi_B')/\omega \tag{8}$$

The value of $V_{mix}$ is averaged over a plurality of measurement intervals, e.g., ten, yielding an average value, $V_{mixavg}$. From the average, a $\Phi_B$ value is determined, based on the following relationship:

$$\Phi_B = -ARCTAN(\omega * V_{mixavg}/CO) \tag{9}$$

The start of the measurement interval is then adjusted by $\Phi_B$ for the next measurement interval during which a value of cardiac output is determined, compensated for temperature drift and mixing volume delay. This approach works if the mixing volume is not rapidly changing by any significant degree; further, the approach is similar to averaging phase angle for many cycles in order to determine the best measurement interval, but has the following advantage. When averaging phase for several cycles, it is assumed that both the cardiac output and the mixing volume are not rapidly changing over the averaging period, whereas, when averaging mixing volume to determine its compensation, it is only assumed that the mixing volume is not changing very rapidly.

The determination of cardiac output as provided in block 136b uses the relative phase information between the input and blood temperature signal, which can also be used to calculate the phase angle associated with the time delay due to mixing volume, $\Phi_B$, and the phase angle associated with the time delay due to transport, $\Phi_C$. Once the total time delay is determined or its corresponding phase angle, a block 144a provides for shifting the relative input signal phase angle to compensate for the total time delays so that the relative starting point of the input power signal is shifted by the sum of the phase angles $\Phi_A$, $\Phi_B$, and $\Phi_C$. Alternatively, instead of shifting the relative input signal phase angle, the start of the measurement interval can be shifted to compensate for the total time delays, as provided in a block 144b. In either case, the logic illustrated in the flow chart corresponding to block 130 then proceeds in FIG. 10A, with block 132, wherein the cardiac output is displayed. Any shifts made to compensate for the time delays are thus included in the next measurement interval used in determining cardiac output.

The preferred embodiment of the present invention has been described, along with certain modifications, in disclosing the method used to compensate for thermal drift and noise. The description of this method thus far presented has used only a single harmonic (or fundamental) of the repetitive input signal. However, the method can be applied to a complex input power signal with more than one harmonic so that the effects of temperature drift and long-term noise can be minimized in a cardiac output measurement using such an input signal. Thus, it is possible to employ the method with other signal processing techniques used to determine cardiac output, like those of Yelderman or Newbower. In such cases, each harmonic is analyzed separately with a slightly different measurement interval start time. The real components of each detected harmonic in the blood temperature signal can then be added together at the phase angle used for detection to recreate a drift-reduced blood temperature signal, which is subsequently processed as normally done in the technique being employed to determine cardiac output.

While the preferred embodiment of the invention and several modification thereto have been illustrated and described, it will be appreciated that various additional changes can be made therein without departing from the spirit and scope of the invention. Accordingly, it is not intended that the scope of the invention be in any way limited by the disclosure of the preferred embodiment, but instead, that the scope be determined by reference to the claims.

The embodiments of the invention in which an exclusive property or privilege is claimed are defined as follows:

1. A method for measuring cardiac output of a heart that is compensated for a drift in a baseline temperature of blood, comprising the steps of:
   (a) producing a periodically varying input signal that is used for changing a temperature of blood within the heart, so that a temperature of the blood leaving the heart varies periodically with respect to the baseline temperature of the blood;
   (b) sensing the temperature of the blood leaving the heart, producing a blood temperature signal corresponding thereto that varies periodically;
   (c) filtering the blood temperature signal to determine a filtered output signal comprising an in-phase component and a quadrature component;
   (d) selecting a measurement interval for the blood temperature signal relative to the input signal, so as to insure that the filtered output signal predominantly comprises the in-phase component; and
   (e) determining the cardiac output of the heart as a function of the input signal and of the filtered output signal, the effect of any baseline temperature drift being minimized in this determination because the baseline temperature drift primarily comprises the quadrature component, which is substantially out of phase with the in-phase component of the filtered output signal.

2. The method of claim 1, wherein the step of selecting the measurement interval comprises the step of shifting a time at which the input signal is applied relative to a measurement interval of the blood temperature signal that was initially arbitrarily selected.

3. The method of claim 1, wherein the step of selecting the measurement interval comprises the step of shifting the measurement interval during which the blood temperature signal is filtered so that it is at a predefined phase angle with respect to the input signal.

4. The method of claim 3, wherein the phase angle by which the measurement interval is shifted relative to the input signal is selected as a function of a phase lag associated with a thermal mass of apparatus inserted into the heart to periodically vary the temperature of the blood by application of the input signal, and as a function of a phase lag associated with a thermal mass of a temperature sensor used to sense the temperature of the blood leaving the heart.

5. The method of claim 3, wherein the phase angle by which the measurement interval is shifted relative to the input signal is selected as a function of a phase lag caused by a mixing volume of the heart.

6. The method of claim 5, wherein the step of filtering comprises the step of determining a phase angle of the blood temperature signal in a frequency domain, wherein the phase lag caused by the mixing volume is determined by averaging the phase angle of the blood temperature signal over a plurality of measurement intervals to determine an average phase angle, and wherein the amount by which the measurement interval is shifted in phase is chosen as necessary to make the average phase angle of the blood temperature signal substantially equal to zero.

7. The method of claim 5, wherein the phase lag of the mixing volume is determined by the steps of performing a spectral analysis of the filtered output signal over a plurality of measurement intervals to determine a phase angle for the filtered output signal in a frequency domain; and, adjusting the measurement interval so said phase angle is substantially equal to zero.

8. A method for measuring cardiac output of a heart so as to compensate for a drift in a baseline temperature of blood and for other noise, comprising the steps of:
   (a) producing a periodic input signal that changes a temperature of blood leaving the heart with respect to the baseline temperature of blood entering the heart, said input signal comprising a wave form defining a plurality of cycles, each cycle extending over a predefined period of time;
   (b) sensing the temperature of blood leaving the heart, producing a blood temperature signal that varies periodically in a manner corresponding to the period of the input signal, said blood temperature signal comprising a wave form defining a plurality of cycles, each cycle extending over the predefined period of time;
   (c) providing a selected phasal relationship between a start of the input signal and a start of a measurement interval during which the blood temperature signal is produced, so that the drift in the baseline temperature of blood and other noise add to the blood temperature signal in quadrature; and
   (d) determining the cardiac output of the heart as a function of the input signal and of the blood temperature signal, any effect of the baseline temperature drift and other noise being minimized in this determination because any contribution of the baseline temperature drift and noise to the blood temperature signal is substantially out of phase with changes in the blood temperature signal caused by the input signal and is therefore substantially negligible.

9. The method of claim 8, wherein the step of providing a selected phasal relationship comprises the step of shifting a starting point during a cycle of the periodic input signal relative to an initial starting point so that the baseline temperature of blood and other noise add to the blood temperature signal in quadrature, a point initially selected for the start of the measurement interval in each cycle of the blood temperature signal remaining unchanged.

10. The method of claim 8, wherein the step of determining the cardiac output of the heart comprises the steps of digitizing the blood temperature signal to produce a corresponding digital blood temperature signal; and filtering the digital blood temperature signal to determine an in-phase component and a quadrature component together comprising a filtered output signal, a point during each cycle of the blood temperature signal being selected for the start of the measurement interval, which is equal in duration to the predefined period of time for each cycle, so that the blood temperature signal contributes principally to the in-phase component and the baseline temperature drift and other noise contribute principally to the quadrature component.

11. The method of claim 10, wherein the step of filtering comprises the step of performing a discrete Fourier transform of the digital blood temperature signal to determine the in-phase and the quadrature components of the digital blood temperature signal.

12. The method of claim 10, further comprising the steps of spectrally analyzing a plurality of cycles of the filtered output signal to determine an average phase angle of the filtered output signal; and selecting a point during each cycle of the blood temperature signal so as to insure that the average phase angle of the filtered output signal is substantially equal to zero.

13. The method of claim 10, further comprising the steps of spectrally analyzing a plurality of cycles of the filtered output signal to determine an average phase angle of the filtered output signal; and selecting the start of the input signal so as to insure that the average phase angle of the filtered output signal is substantially equal to zero.

14. The method of claim 10, wherein the periodic input signal comprises a plurality of harmonic frequencies, further comprising the steps of:
  (a) providing a selected phasal relationship between the start of the input signal and the start of the measurement interval for each of the harmonic frequencies each such measurement interval starting a different phasal time than the measurement intervals of any other harmonic frequencies;
  (b) determining an in-phase component of the blood temperature signal for each of the measurement intervals;
  (c) adding the in-phase components for each of the measurement intervals of the harmonic frequencies together to produce the filtered output signal; and
  (d) using the filtered output signal to determine the cardiac output, said cardiac output being compensated for the baseline temperature drift and noise.

15. The method of claim 10, wherein the step of providing a selected phasal relationship comprises the step of determining a time delay to compensate for a time constant of a mixing volume and for a transport delay, both of which are characteristic of the heart.

16. The method of claim 15, wherein the filtered output signal includes a magnitude and a phase angle, and wherein compensation for the time constant of the mixing volume and the transport delay is determined by calculating an average phase angle of the filtered output signal over a plurality of cycles and shifting a point during each cycle of the blood temperature signal at which the measurement interval starts as necessary to make the average phase angle of the filtered output signal substantially equal to zero.

17. The method of claim 15, wherein the filtered output signal includes a magnitude and a phase angle, and wherein compensation for the time constant of the mixing volume and the transport delay is determined by calculating an average phase angle of the filtered output signal over a plurality of cycles and shifting a start of the input signal as necessary to make the average phase angle of the filtered output signal substantially equal to zero.

18. The method of claim 8, wherein the step of producing the periodic input signal comprises the steps of supplying a sinusoidally varying electrical current to a resistance heater disposed in the heart, which transfers heat to the blood to periodically change its temperature in a sinusoidal manner.

19. The method of claim 8, wherein the step of producing the periodic input signal comprises the steps of periodically supplying a temperature-conditioned fluid to a heat exchanger disposed in the heart, the heat exchanger modifying the temperature of the blood in the heart by transferring heat between the temperature-conditioned fluid and the blood.

20. The method of claim 8, wherein the step of providing a selected phasal relationship comprises the step of determining a time delay for either the start of the measurement interval or the start of the input signal, said time delay including a compensation for a time constant of a temperature sensor that produces the blood temperature signal.

21. The method of claim 8, further comprising the steps of:
  (a) determining a cardiac output that is not compensated for the baseline temperature drift;
  (b) estimating a mixing volume phase angle;
  (c) determining a mixing volume as a function of the mixing volume phase angle and of the cardiac output that is not compensated for the baseline temperature drift;
  (d) averaging the mixing volume over a plurality of measurement intervals to determine an average mixing volume;
  (e) determining a mixing volume phase angle as a function of the average mixing volume and the cardiac output that is not compensated for the baseline temperature drift; and
  (f) adjusting the phasal relationship between the start of the input signal and the start of the measurement intervals during subsequent determinations of the cardiac output as a function of the mixing volume phase angle and to compensate for the drift in the baseline temperature and other noise.

* * * * *